(12) United States Patent
Jung et al.

(10) Patent No.: US 9,337,675 B2
(45) Date of Patent: May 10, 2016

(54) INDUCTIVE CHARGER FOR HAND HELD APPLIANCES

(71) Applicant: Braun GmbH, Kronberg (DE)

(72) Inventors: Philipp Jung, Kronberg (DE); Ivo Kunath, Neukirch (DE); Herbert Petzold, Wiesbaden (DE); Martin Stratmann, Kronberg (DE)

(73) Assignee: Braun GmbH, Kronberg (DE)

( * ) Notice: Subject to any disclaimer, the term of this patent is extended or adjusted under 35 U.S.C. 154(b) by 563 days.

(21) Appl. No.: 13/749,732

(22) Filed: Jan. 25, 2013

(65) Prior Publication Data

US 2013/0193915 A1    Aug. 1, 2013

(30) Foreign Application Priority Data

Jan. 27, 2012   (EP) ..................................... 12152947

(51) Int. Cl.

| | | |
|---|---|---|
| *H02J 7/00* | (2006.01) | |
| *A61C 17/22* | (2006.01) | |
| *H02J 7/02* | (2016.01) | |
| *H02J 5/00* | (2016.01) | |

(52) U.S. Cl.
CPC ............. *H02J 7/0044* (2013.01); *A61C 17/224* (2013.01); *H02J 7/025* (2013.01); *H02J 5/005* (2013.01)

(58) Field of Classification Search
CPC ...... A61C 17/224; H02J 7/025; H02J 7/0044; H02J 5/005
See application file for complete search history.

(56) References Cited

U.S. PATENT DOCUMENTS

| | | | | |
|---|---|---|---|---|
| 6,417,645 | B1 * | 7/2002 | Yamaguchi et al. | 320/115 |
| 6,581,233 | B1 * | 6/2003 | Cheng | 15/28 |
| 7,210,940 | B2 * | 5/2007 | Baily et al. | 439/38 |
| 7,211,986 | B1 * | 5/2007 | Flowerdew | 320/108 |
| 7,414,380 | B2 * | 8/2008 | Tang et al. | 320/108 |
| 7,748,070 | B2 * | 7/2010 | Chan et al. | 15/22.1 |
| 7,917,982 | B2 * | 4/2011 | Kressner et al. | 15/22.1 |
| 7,994,436 | B2 * | 8/2011 | Yamamoto et al. | 174/520 |
| 8,810,196 | B2 * | 8/2014 | Ettes et al. | 320/108 |
| 2008/0209650 | A1 * | 9/2008 | Brewer et al. | 15/22.1 |
| 2009/0278523 | A1 * | 11/2009 | Yoda et al. | 323/318 |
| 2010/0156193 | A1 * | 6/2010 | Rhodes et al. | 307/104 |
| 2010/0219183 | A1 * | 9/2010 | Azancot et al. | 219/676 |
| 2011/0163714 | A1 * | 7/2011 | Ettes et al. | 320/108 |
| 2014/0111147 | A1 * | 4/2014 | Soar | 320/108 |

FOREIGN PATENT DOCUMENTS

| | | |
|---|---|---|
| DE | 195 13 539 A1 | 10/1996 |
| DE | 20 2006 013664 U1 | 11/2006 |
| EP | 0 642 203 A1 | 3/1995 |
| JP | 11 098707 A | 4/1999 |
| WO | WO 2011/091528 A1 | 8/2011 |

OTHER PUBLICATIONS

European Search Report for EP 12 15 2947 dated Jun. 9, 2012.

* cited by examiner

*Primary Examiner* — Naum B Levin
(74) *Attorney, Agent, or Firm* — Alexandra S. Anoff

(57) ABSTRACT

An inductive charger for charging a hand-held appliance is disclosed. The inductive charger includes a charger coil surrounding a magnetic core, the magnetic core forming at least a part of a charger projection, wherein the charger projection is surrounded by the charger coil which is adapted to be inserted, together with the charger projection of the magnetic core, into a charging recess of the hand-held appliance.

15 Claims, 3 Drawing Sheets

INDUCTIVE CHARGER FOR HAND HELD APPLIANCES

FIELD OF THE INVENTION

The present disclosure generally relates to inductive chargers for hand-held appliances such as personal care appliances. More particularly, the present disclosure relates to an inductive charger for charging a toothbrush or a shaver, including a charger coil surrounding a magnetic core, the magnetic core forming a charger projection adapted to be inserted into a charging recess of the hand-held appliance.

BACKGROUND OF THE INVENTION

Electric toothbrushes sometimes use rechargeable batteries or accumulators accommodated within the housing of a handpiece of the toothbrush. For recharging the batteries in the handpiece, sometimes inductive chargers are used so as to avoid the problems going along with mechanical electric connectors and use thereof in wet and humid conditions. To allow inductive charging, the handpiece may include a secondary coil extending around a charging recess which may be provided in the bottom part of the toothbrush handpiece so as to be pushed onto a thorn-like or mandrel-like charger projection. Such charger projection may be provided on a top surface side of a base part and, aside from charging, may serve as a holding element for holding and storing the toothbrush handpiece in a substantially upright position. Such charger projection of the base part may include a portion of a magnetic core which cooperates with a charger coil in the base part so as to bundle and transfer the magnetic flux to the secondary coil provided in the toothbrush handpiece when said handpiece is set atop the base part with the secondary coil neighboring the magnetic core of the base part's charger coil.

When using such charger devices for charging rechargeable batteries in the handpiece of a hand-held appliance such as a toothbrush, the space available for inserting the charger projection of the inductive charger into the charging recess of the handpiece is rather limited since the outer dimensions of the handpiece are determined by ergonomic requirements since the handpiece should in particular be easily and comfortably grippable. In particular, when it is desired to provide the charging recess in the bottom part of the handpiece, the available space and the possible diameter of such recess is rather limited what may result in rather slim and small charger projections not allowing for transfer of as much energy as may be desirable. Nevertheless, so as to allow for acceptable charging times, rather large and bulky charger coils and corresponding supply equipment are used so as to be able to provide the necessary magnetic flux. The charging efficiency is limited due to undesired energy dissipation and losses.

SUMMARY OF THE INVENTION

In one embodiment, an inductive charger for charging a hand-held appliance is provided. The inductive charger includes a charger coil surrounding a magnetic core, the magnetic core forming at least a part of a charger projection, wherein the charger projection is surrounded by the charger coil which is adapted to be inserted, together with the charger projection of the magnetic core, into a charging recess of the hand-held appliance.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
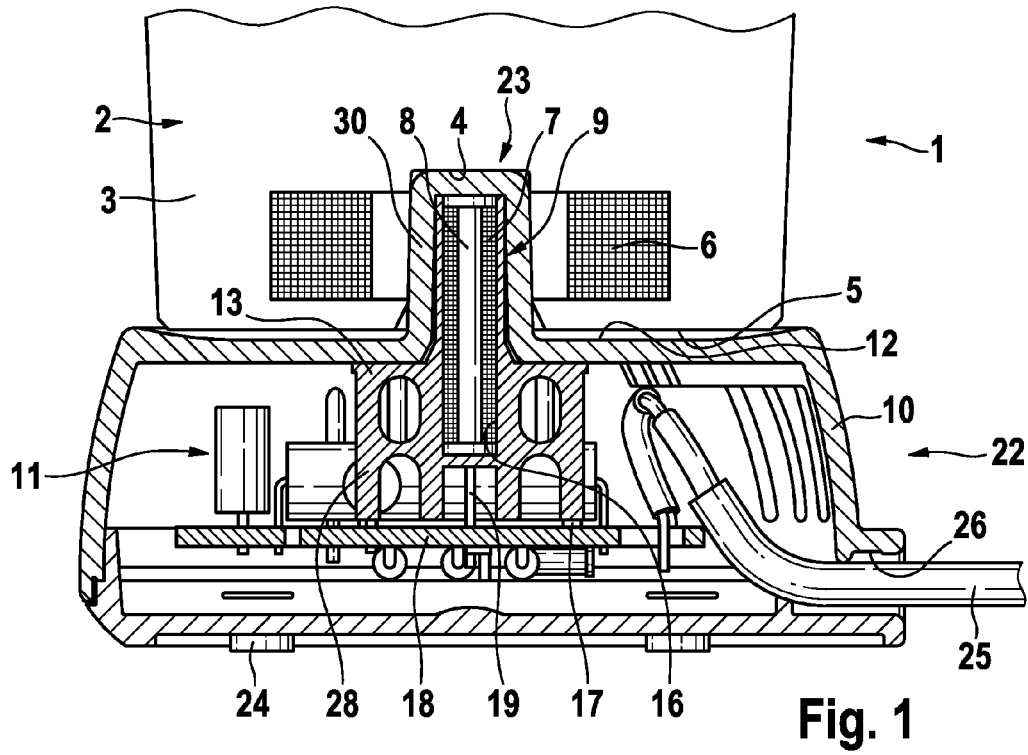
FIG. 1: a cross-sectional view of an inductive charger for charging the handpiece of an electric toothbrush according to embodiments shown and described herein, wherein the inductive charger is shown to have a charger projection inserted into a charging recess provided in the bottom part of the handpiece of the toothbrush.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

To allow for a high coupling factor and an efficient energy transfer with low losses during the charging process, the charger coil of the inductive charger surrounds the projecting portion of the magnetic core so that it is not only the projecting portion of the magnetic core, but also at least a part of the charger coil that can be inserted into the charging recess provided in the handpiece of the hand-held appliance. The insertion of at least a part of the charger coil, together with the projecting portion of the magnetic core, into the charging recess of the appliance's handpiece increases the magnetic flux that is applied to the secondary coil of the hand-held appliance even if the charging power is reduced in comparison to charger devices where only a projecting portion of the magnetic core is inserted into the charging recess with the charger coil not being inserted into said charging recess, but only surrounding the magnetic core at a portion adjacent the projecting portion. To better use the effects provided by the charger coil extending around the projecting portion of the magnetic core to be inserted into the charging recess, the hand-held appliance may include a secondary coil that extends around the charging recess so that the charger coil extends at least in part into the space surrounded by the secondary coil and has an axial overlap with the secondary coil when the hand-held appliance is in its charging position, i.e. is set atop the inductive charger and the charging projection thereof.

The charger coil extending around the projecting portion of the magnetic core may be directly wound around the magnetic core and/or may have direct contact to the peripheral surface of the magnetic core. A gap-free arrangement of the charger coil on the magnetic core achieves a size and diameter of the coil/core assembly as small as possible, thereby allowing for inserting the charger coil into the charging recess of the hand-held appliance even when the charging recess is limited in size and diameter. In addition to such reduced dimensions, the charger coil is exactly positioned relative to the magnetic core, wherein position tolerances due to gaps or separating layers between the charger coil and the magnetic core can be eliminated.

The magnetic core, in particular, the projecting portion thereof to be inserted into the charging recess of the hand-held appliance, may be made of ferrite and/or may have an elongate, for example, pin-like or cylindrical shape, wherein an end portion of the magnetic core may be provided with an increased diameter portion, for example, in terms of a radially extending flange and/or a collar, so as to facilitate winding of the charger coil around the magnetic core. The magnetic coil may be formed by a copper wire winding around the magnetic core.

According to another aspect of the present disclosure, the core/charger coil-assembly may be held in place by a supporting body which may be formed as a separate piece that can be mounted to a housing for accommodating at least a part of the supply means for supplying the charger coil with electric power. Such housing may form a base part for storing the hand-held appliance when the appliance is not used, wherein such base part may include a foot surface so that the base part can stand on a table or a bathroom shelf. Furthermore, the base part may include holding means for holding the hand-held appliance in a storage position which may be an upright position, wherein such holding means may be associated with and/or formed by a housing portion surrounding such charger projection of the magnetic core/charger coil assembly. In one embodiment, the housing of the inductive charger may include a thorn-like or mandrel-like, typically generally cylindrical projection extending from a top side surface of the housing, such thorn-like projection being insertable into the charging recess of the hand-held appliance which charging recess may have a dead end bore shape. The charger coil/ magnetic core assembly of the inductive charger may extend into the thorn-like projection of the housing, wherein the housing projection and the charging recess in the hand-held appliance may be adapted to each other in shape and/or in dimension so as to allow for holding the hand-held appliance in a storage position by means of form-fitting and/or slightly press-fitting the charging recess onto the projection. The charger coil, together with the surrounded magnetic core may be received and held in place within such housing projection forming the holding means for holding the handpiece of the appliance in a storing and/or charging position.

In order to achieve exact positioning of the charger coil/ magnetic core assembly, a supporting body holding the magnetic core in a fixed, rigid manner may extend along the inner surface of a top side housing wall and/or may be mounted to such top side housing wall. In particular, such supporting body may be formed as a separate piece to which the magnetic core and/or the pre-assembled magnetic core/charger coil assembly may be mounted so that the pre-assembled structure comprising the supporting body, the magnetic core and the charger coil and optionally other components for supplying power to the charger coil, may be mounted in an interior space of the housing with the charger coil and the magnetic core being held in exact position.

Such supporting body may include a receiving recess for receiving a portion of the magnetic core wherein such receiving recess may have a substantially cylindrical or conical shape and/or a dead-end bore structure. Such receiving recess may be adapted to the magnetic core in shape and/or in dimension so as to hold the magnetic core in a defined position relative to the supporting body. In particular, a form-fitting and/or press-fitting engagement of the magnetic core with the receiving recess may be provided. In addition or in the alternative, an adhesive bonding may be provided so as to rigidly secure the magnetic core to the supporting body.

The supporting body may include at least one supporting flange or supporting wing which may be substantially plate-shaped and may extend from the holding portion holding the magnetic core in a direction substantially perpendicular to the longitudinal extension of the magnetic core. In accordance with an embodiment, a pair of such supporting wings may extend to opposite sides of the magnetic core.

The at least one wing may include at least one engagement portion adapted to engage with a housing portion so as to provide for exact positioning and support of the magnetic core relative to the charger housing. The engagement portion may include a contact surface for contacting an interior surface of a top side wall portion of the housing, thereby preventing the supporting body and the magnetic core attached thereto from pivoting movements and/or axial movements that would detrimentally affect the desired registering of the magnetic core/charger coil with the secondary coil in the hand-held appliance.

In the alternative or in addition to such contact surfaces, the supporting body may include at least one press-fitting and/or form-fitting recess or projection cooperating with at least one projection or recess of the housing of the charger. By means of such form-fitting and/or press-fitting of the supporting body within the charger housing, the magnetic core including the charger coil wound around such core can be exactly positioned relative to the holding means for holding the hand-held appliance in its storage and/or charging position.

In one embodiment, the supporting body to which the magnetic core is attached may include another supporting portion for supporting a circuit board which may be provided for supplying electric power to the charger coil and/or providing control thereof. According to One embodiment, the supporting body may provide for support and electrical connection of the circuit board. For example, the supporting body may be provided with electrical connectors for connecting the charger coil with the circuit board. In another example, such electrical connectors may include a pair of connector pins which may extend through and/or held in place by the supporting body, wherein a first end of each connector pin may be connected to a respective end of the charger coil, whereas another end of each of the connector pins may be connected to the circuit board and/or an electrical powering element attached thereto.

The charger coil may be encapsulated and/or shielded against environmental influences such as fluids and humidity or contact with a user's skin by means of an insulating cover, wherein the insulating cover may include a molded insulating layer such as an insulating resin applied to the charger coil by means of, for example, a varnishing or impregnating process. In the alternative or in addition to such molded insulating layer, the insulating cover may include a sleeve-shaped covering cap that may be connected to the supporting body at an edge portion of the covering cap. The insulating cover may in particular be present in addition to a housing projection into which the assembly of magnetic core, charging coil and insulating cover extends.

Thus, even in a case where the housing projection breaks open (for example, when the inductive charger falls to the ground), the charging coil is still covered by the insulating cover and a user is protected from the voltage that may be present across the charging coil.

As can be seen from FIG. 1, the inductive charger may be part of a base station 22 that may store the hand-held appliance 1 when not in use. The hand-held appliance 1 can be an electric toothbrush 2 which includes a handpiece 3 to which a brush head or other attachments such as interdental cleaners may be attached. In the alternative to such toothbrush 2, the invention also can be applied to other personal care appliances such as shavers, body hair removers or other hand-held appliances which include rechargeable batteries or accumulators for powering functional components of the appliance. In an electric toothbrush 2, such functional powering means may include driving means for driving the brush head of the toothbrush, wherein such drive means and/or the rechargeable batteries may be accommodated within the housing of the handpiece 3. To allow inductive charging of such rechargeable batteries, the handpiece 3 of the hand-held appliance 1 may further include a secondary coil 6 which may be positioned to surround at least in part a charging recess 4 which may be provided in the bottom part 5 of the handpiece 3, as shown in FIG. 1. Such charging recess 4 may have a central position within said bottom part 5 and may have a cup shape, more particularly a shape like a in particular cylindrical dead end bore or the like.

Figure 2:
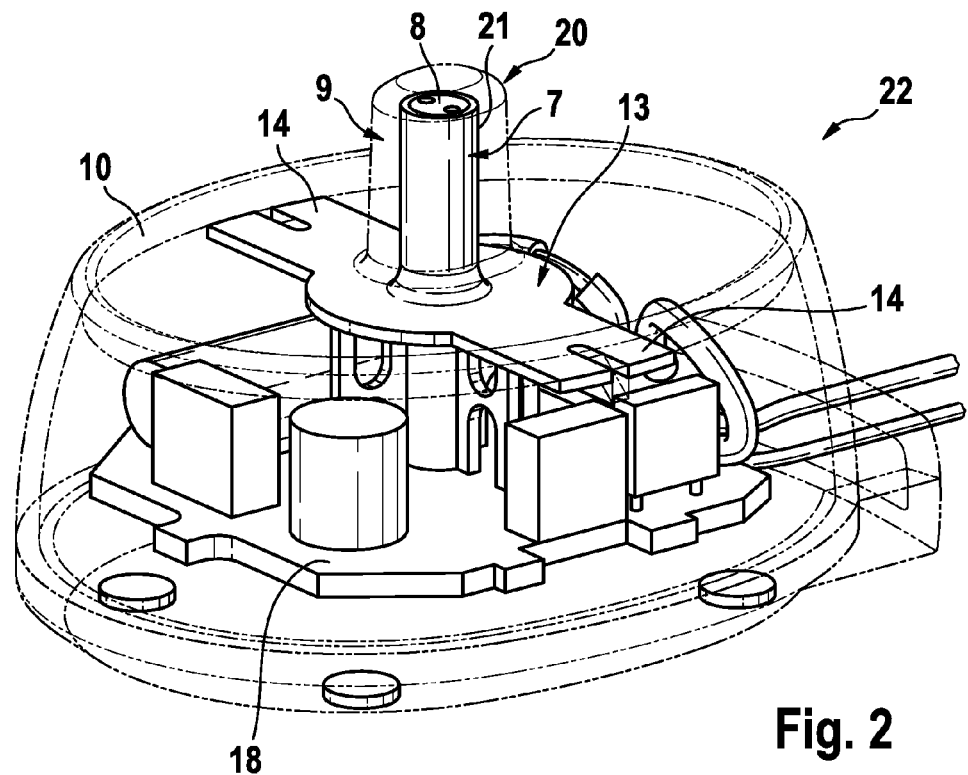
FIG. 2: a perspective view of the inductive charger of FIG. 1, wherein a supporting body is shown as attached to a charger housing, the supporting body holding the magnetic core and the charger coil in exact position and providing for mechanical and electrical connection of the charger coil to a circuit board.

The base station 22 shown in FIGS. 1 and 2 may include holding means 23 for holding the handpiece 3 of appliance 1 in an upright position when storing the appliance 1, wherein the holding means 23 may be formed by a part of a charger housing 10 and/or a part of the inductive charger elements. As can be seen from FIGS. 1 and 2, the charger housing 10 may include a thorn-like or mandrel-like, typically generally cylindrical projection 30 extending from a substantially planar and/or horizontally oriented top side surface 12 wherein the longitudinal extension of said projection may be substantially upright. Together with some of the functional charger elements in the interior of housing 10, the projection forms a charger projection 9 onto which the handpiece 3 may be put with the charging recess 4 so that the charger projection 9 extends within the charging recess 4. The outer dimension and shape of the charger projection 9 may be adapted to the inner dimensions and shape of the recess 4 to create a form-fitting and/or slightly press-fitting engagement to hold the handpiece 3 in an upright position onto the base station 22.

On its bottom side, the housing 10 is shown to have foot elements 24 so that the base station 22 is able to stand safely on a table or a bathroom shelf.

In the interior of housing 10, the functional components of the charger are accommodated, such functional components including a charger coil 7 wound about a substantially pin-shaped magnetic core 8 which may be made of ferrite material and may have an elongate shape. Furthermore, housing 10 may accommodate supply means for supplying the charger coil 7 with electric current, wherein such supply means may include a (printed) circuit board 18 onto which controlling elements and/or supply elements such as capacitors, resistors, relays, transistors or a control unit which may include a microprocessor etc. can be mounted. Electric power may be supplied to the circuit board 18 and/or the elements mounted thereon via a power cord 25 which may be connected to the supply means in the interior of housing 10 and may exit said housing 10 through an opening 26, as shown in FIG. 1.

Figure 3:
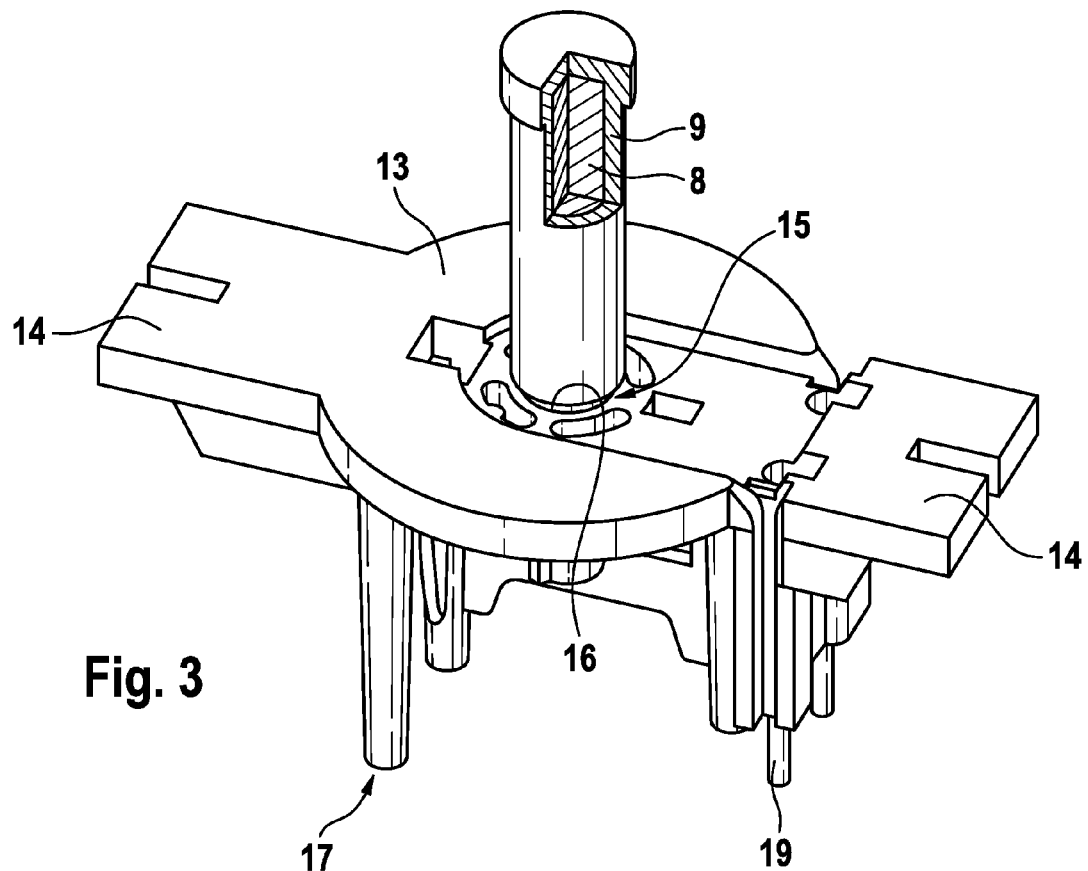
FIG. 3: a perspective, partly cross-sectional view of the mounted assembly of the supporting body and the coil core structure attached thereto.

As shown by FIGS. 1, 2 and 3, the magnetic core 8 may be held by a separate supporting body 13 which is received within the interior of housing 10 and may be attached thereto as will be described. A central portion of said supporting body 13 may include a holding recess 15 which is adapted in shape and dimension to the magnetic core 8 and/or the charger coil 7 wound around the magnetic core 8, wherein a form-fitting and/or slightly press-fitting engagement of the magnetic core 8 with the holding recess 15 may be provided. In addition or in the alternative, the magnetic core 8 may be glued or bonded to the supporting body 13 in an adhesive manner, wherein other bonding or fixation means may be used to rigidly fix the magnetic core 8 to the supporting body 13.

As can be seen from FIGS. 2 and 3, the supporting body 13 which may be made from plastic, for example, in an injection molding process, may include a pair of supporting wings 14 extending to opposite sides of the holding recess 15. An upper side of the supporting wings 14 may be adapted to the shape and contours of the inner surface of the top side wall portion of the housing 10 so as to allow for positioning of the supporting body 13 relative to the housing 10 by means of contacting the interior surfaces of the top side wall with the surfaces of the supporting wings 14. As shown by the Figures, the top side wall portion of housing 10 may have a substantially planar configuration so that the supporting wings 14 may extend substantially perpendicular to the longitudinal direction of the magnetic core 8 and/or may have also a planar configuration.

Figure 5:
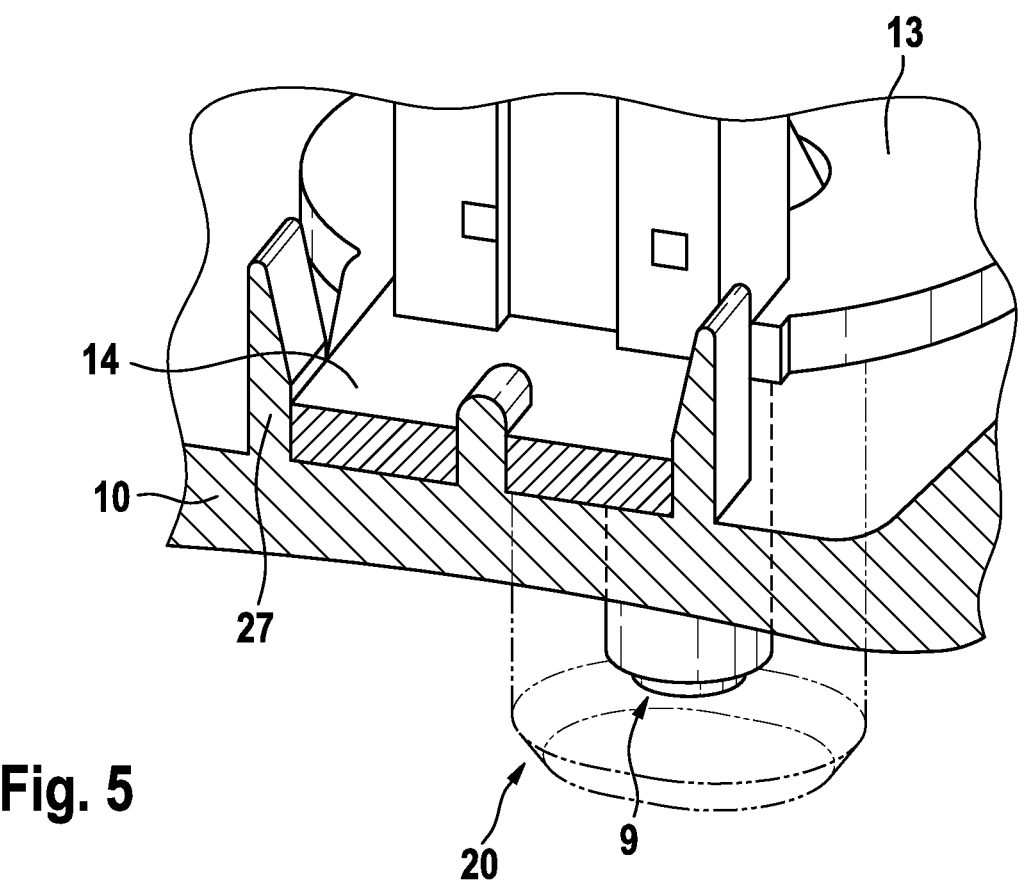
FIG. 5: a perspective fragmentary up side down view of the connection of the supporting body and the connection thereof to the charger housing.

To allow for precise positioning of the supporting body 13, the housing 10 and/or the supporting body 13, for example, the supporting wings 14 may include form-fitting and/or press-fitting contours in terms of, for example, recesses and projections which may engage with each other as shown by FIG. 5. For example, the supporting wings 14 may include a slot-shaped recess which may engage with a web-shaped projection of housing 10, wherein the housing 10 may include, in addition to or in the alternative lateral edges 27 between which the wings 14 may be positioned and/or clamped, as shown in FIG. 3.

Furthermore, the supporting body 13 may include a supporting portion 17 for supporting and/or holding the aforementioned circuit board 18, wherein such supporting portion 17 may include holding flanges 28 projecting from the aforementioned supporting wings 14 and/or may form a central portion of the supporting body 13. The supporting portion 17 may be adapted to hold the circuit board 18 in a position substantially perpendicular to the longitudinal extension of the magnetic core 8 at a certain distance spaced apart therefrom.

The supporting body 13 together with the magnetic core 8 and the charger coil 9 and optionally also together with the circuit board 18 may form a preassembled structure. In one embodiment, the magnetic core 8 may be attached to the supporting body 13 as well as electrical connectors 19 which may include connector pins can be attached to the supporting body 13. The copper wire forming charger coil 9 may be attached to one of such electrical connectors 19 and may then be wound around the magnetic core 8 to form at least one or a plurality of charger coil layers. The other end of the copper wire may then be connected to the other electrical connector 19, wherein electrical connection between the wire and the connectors 19 may be provided, for example, by means of soldering.

Figure 4:
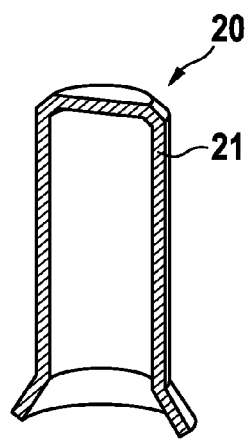
FIG. 4: a cross-sectional cut through an insulating cap for covering the coil core structure.

To protect the charger coil 7 wound around the magnetic core 8 from environmental influences and also to protect a user from contact with the high voltage that may be present at the charger coil 7, an insulating cover 20 may be provided which may include a molded insulating layer which may be applied over the charger coil 7, e.g., in an impregnating process. In the alternative or in addition to such molded insulating layer, an insulating cap 21 which may be formed, e.g., by injection molding from a thermoplastic material, may be used, wherein such insulating cap 21 may have a sleeve-like shape as shown in FIG. 4 so that the magnetic core 8 including charger coil 7 wound therearound can be hooded with said insulating cap 21. Said insulating cap 21 may be connected to the supporting body 13 at the edge portion of the cap 21 at an open end thereof.

It is to be noted here that the use of an insulating cover is in general considered to have a certain effect, namely to provide a further protection (and insulating) cover in case that the housing projection may break open, for example, when it falls down to the floor. Insofar, it is considered as a particular feature to have a charging projection comprising a magnetic core around which at least partly a charging coil is wound and a further insulating cover that covers at least the wire of the charging coil. This assembly comprising the magnetic core, the charging coil and the insulating cover is accommodated in a housing projection as discussed above.

As can be seen from FIGS. 1, 2 and 3, the magnetic core 8 including the charger coil 7 projects from the supporting body 13 into the projection formed by housing 10. More particularly, the magnetic core/charger coil assembly extends substantially perpendicular from the upper surface of the supporting body 13 to extend into the housing projection at the top side thereof and to form charger projection 9. Thus, charger coil 7, together with magnetic core 8 can be inserted into the charging recess 4 provided in the end face 5 of handpiece 3, as shown in FIG. 1.

Due to winding the charger coil 7 directly onto the ferrite core 8, the inductive element of the charger may have a very slim and compact design with a rather small diameter that allows to insert also the charger coil 7 into the charging recess 4 of handpiece 3. Since the charger coil 7 may be inserted into the charging recess 4 of handpiece 3 and more particularly within the interior space surrounded by the secondary coil 6 of handpiece 3, the coupling factor between the charger coil 7 and the secondary coil 6 may be increased. Such improved coupling factor allows for minimizing the circuitry supplying electric power to the charger coil 7, thus achieving an advantageous circuit board design.

Furthermore, the transfer of energy can be achieved with a minimized amount of materials for the magnetic core and the charger coil, in particular a reduced amount of copper wire and ferrite for the core.

Such reduced amount of copper wire also provides for advantages relative to the impregnating and/or sealing process by means of which the conveying components of the electrical elements are protected against humid environment. For such impregnating processes, two-components systems may be used to solidify or harden within short time in an exothermic reaction. Such molding process to apply an insulating layer onto the charger coil may be disturbed by air which is trapped in said charger coil, in particular when said charger coil includes a plurality of layers. The entrapped air discharges during the molding process and may create channels extending through the insulating layer, thus reducing security. Due to the aforementioned reduction of the necessary amount of copper wire, such difficulties resulting from entrapped air are reduced.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An inductive charger for charging a hand-held appliance comprising:
   a charger coil surrounding a magnetic core, the magnetic core forming at least a part of a charger projection, wherein the charger projection is surrounded by the charger coil which is adapted to be inserted, together with the charger projection of the magnetic core, into a charging recess of the hand-held appliance;
   wherein a housing is provided for accommodating at least a part of electric supply means connected to said charger coil, said housing having a top side surface surrounding said charger projection which projects from said top side surface in a direction substantially perpendicular thereto forming a thorn-like or mandrel-like, cylindrical housing projection;
   wherein the charger coil is covered by an insulating cover, said insulating cover comprising a sleeve-shaped insulating cap that is connected at an edge portion with the supporting body, the insulating cover being present in addition to the housing projection into which the assembly of magnetic core, charger coil and insulating cover extends.

2. The inductive charger according to claim 1, wherein the charger coil is directly contacting a peripheral surface of the charger projection of the magnetic core.

3. The inductive charger according to claim 1, wherein the charger coil is, at least in part, received and held in place within the interior of a housing projection forming holding means for holding the hand-held appliance in a predetermined storage and/or charging position.

4. The inductive charger according to claim 1, wherein the magnetic core is supported by and/or rigidly fixed to a supporting body adapted to extend along a top side housing wall portion.

5. The inductive charger according to claim 1, wherein the supporting body has at least one, supporting wing extending from a holding portion holding the magnetic core, the supporting wing having at least one engagement portion adapted to engage with a housing portion.

6. The inductive charger according to claim 5, wherein the supporting body is provided with a pair of the supporting wings extending to opposite sides of the magnetic core.

7. The inductive charger according to claim 1, wherein the supporting body and a housing portion include form-fitting and/or press-fitting recesses and projections for holding the supporting body in place by means of engagement of the form-fitting and/or press-fitting recesses and projections with each other.

8. The inductive charger according to claim 1, wherein the supporting body is provided with a central receiving recess for receiving a portion of the magnetic core, the receiving recess being adapted to the magnetic core in shape to hold the magnetic core in a defined position relative to the supporting body.

9. The inductive charger according to claim 1, wherein the supporting body is provided with a supporting portion for supporting a circuit board for providing the charger coil with electric power, the supporting body being provided with electrical connectors for connecting the charger coil with the circuit board.

10. The inductive charger according to claim 9, wherein the electrical connectors include connector pins held in place by and extending through the supporting body, the connector pins, at one side of the supporting body being connected to the charger coil and, at an opposite side of the supporting body being connected to the circuit board.

11. The inductive charger according to claim 1, wherein the charger coil is covered by an insulating cover, the insulating cover including a molded insulating layer connected at an edge portion with the supporting body.

12. The inductive charger according to claim 1, wherein the magnetic core has an elongate, pin-like or cylindrical shape.

13. A hand-held appliance for personal care comprising an inductive charger as defined by claim 1, and further comprising a handpiece including a rechargeable battery which is chargeable by the inductive charger.

14. The hand-held appliance according to claim 13, wherein the handpiece includes a charging recess into which the charger projection of the inductive charger is insertable, wherein the handpiece includes a secondary coil surrounding the charging recess such that the charger coil is, at least in part, received within the interior space surrounded by the secondary coil of the handpiece when the charger projection is inserted into the charging recess.

15. The hand-held appliance according to claim 13, wherein the hand-held appliance is an electric toothbrush.

\* \* \* \* \*